(12) United States Patent
Mohamed et al.

(10) Patent No.: US 9,937,220 B2
(45) Date of Patent: Apr. 10, 2018

(54) ANTI-DIABETIC NUTRACEUTICAL COMPOSITION FROM PALM LEAF EXTRACT

(71) Applicant: UNIVERSITI PUTRA MALAYSIA, Serdang, Selangor Darul Ehsan (MY)

(72) Inventors: Suhaila Mohamed, Serdang (MY); Rosalina Tan Roslan Tan, Serdang (MY)

(73) Assignee: UNIVERSITI PUTRA MALAYSIA, Serdang (MY)

(*) Notice: Subject to any disclaimer, the term of this patent is extended or adjusted under 35 U.S.C. 154(b) by 155 days.

(21) Appl. No.: 14/622,732

(22) Filed: Feb. 13, 2015

(65) Prior Publication Data
US 2015/0157683 A1 Jun. 11, 2015

Related U.S. Application Data

(62) Division of application No. 13/260,188, filed as application No. PCT/MY2009/000041 on Mar. 24, 2009.

(51) Int. Cl.
*A61K 36/889* (2006.01)
*A23L 33/105* (2016.01)

(52) U.S. Cl.
CPC .......... *A61K 36/889* (2013.01); *A23L 33/105* (2016.08); *A23V 2002/00* (2013.01)

(58) Field of Classification Search
None
See application file for complete search history.

(56) References Cited

U.S. PATENT DOCUMENTS 6,984,666 B2  1/2006  Jia et al.

FOREIGN PATENT DOCUMENTS

| DE | 102004018363 A1 * | 11/2005 | ............. A61K 36/06 |
|---|---|---|---|
| EP | 1331858 B1 | 8/2006 | |
| EP | 1738658 A1 | 1/2007 | |
| GB | 2117381 A | 10/1983 | |
| JP | 63-63754 A | 3/1988 | |
| JP | 09-206043 A | 12/1997 | |
| JP | 2000-083654 A | 3/2000 | |
| JP | 2005145948 A * | 6/2005 | |
| WO | 2006/053379 A1 | 5/2006 | |
| WO | 20006/045623 A1 | 5/2006 | |
| WO | 2006/108008 A2 | 10/2006 | |
| WO | 2008/059310 A1 | 5/2008 | |
| WO | 2008/063045 A1 | 5/2008 | |
| WO | 2008/134828 A2 | 11/2008 | |
| WO | 2008/142702 A1 | 11/2008 | |
| WO | 2009/008697 A1 | 1/2009 | |
| WO | 20091051470 A1 | 4/2009 | |

OTHER PUBLICATIONS

Mudaliar, K. "Avarai Nei" from Athmarakshaamirtham, Pub: Ilakkana Achagam, chennai (1897), pp. 536-537. Retrieved from: TKDL on Sep. 8, 2016.*
"Nursing times". "The administration of medicines". Internet publication date: Nov. 19, 2007 [Retrieved from the Internet on: Sep. 9, 2016]. Retrieved from the Internet: <URL: https://www.nursingtimes.net/clinical-archive/medicine-management/the-administration-of-medicines/288560.article>.*
Agasthiyar. "Nilapanai Kirutham" from Agasthiyar Vaithya Rathina Churukkam, Ed. Pub: Thamarai Noolagam, Chennai (1998, 2nd edition), pp. 69-70. Retrieved from: TKDL on Feb. 18, 2017.*
T.P. Trinidad et al., "Glycaemic index of different coconut (*Cocos nucifera*)—flour products in normal and diabetic subjects" British Journal of Nutrition (2003) 90, p. 551-556.
International Search Report dated Jul. 23, 2009 in application No. PCT/MY2009/000041.

* cited by examiner

*Primary Examiner* — Amy L Clark
(74) *Attorney, Agent, or Firm* — Maschoff Brennan

(57) ABSTRACT

A comestible composition with anti-diabetic property which is effective in lowering the blood glucose and help reduce oxidative stress in diabetics and have anti-diabetic properties that protect against diabetic complications, retarding diabetes related organ degeneration and effective to hinder or prevent ailments or conditions resulting from, or exacerbated by, a chronic increase in blood sugar including: tissue degeneration, cardiovascular disease, kidney degeneration, loss of cognitive function, weight loss, visual impairment, and vasomotor symptoms which contains extract from palm leaf.

10 Claims, 5 Drawing Sheets

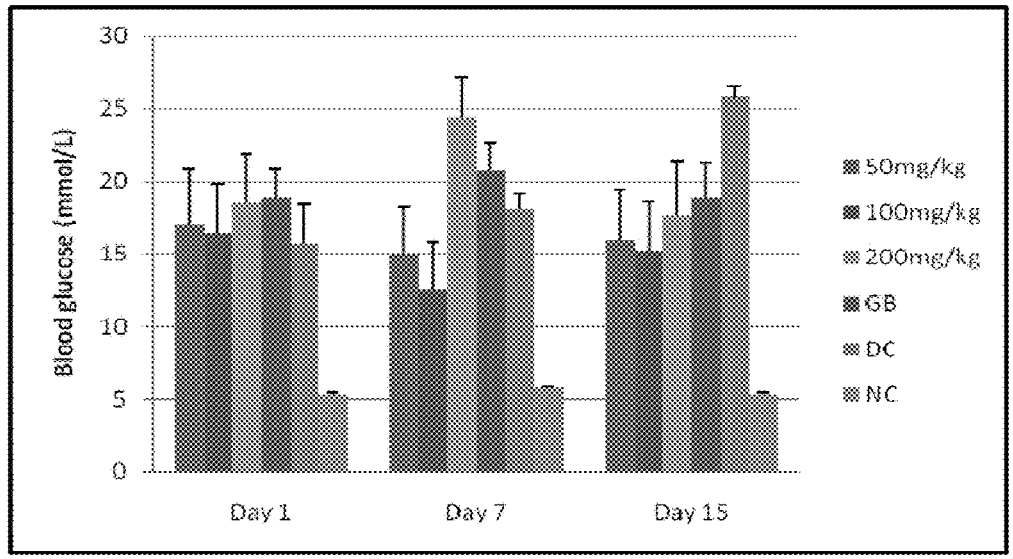

50-200 mg/kg = Palm leaf Extract given to diabetic rats per day
GB = Glibenclamide treated diabetic rats
NC = Normal control Rats        DC = Diabetic negative control untreated rats

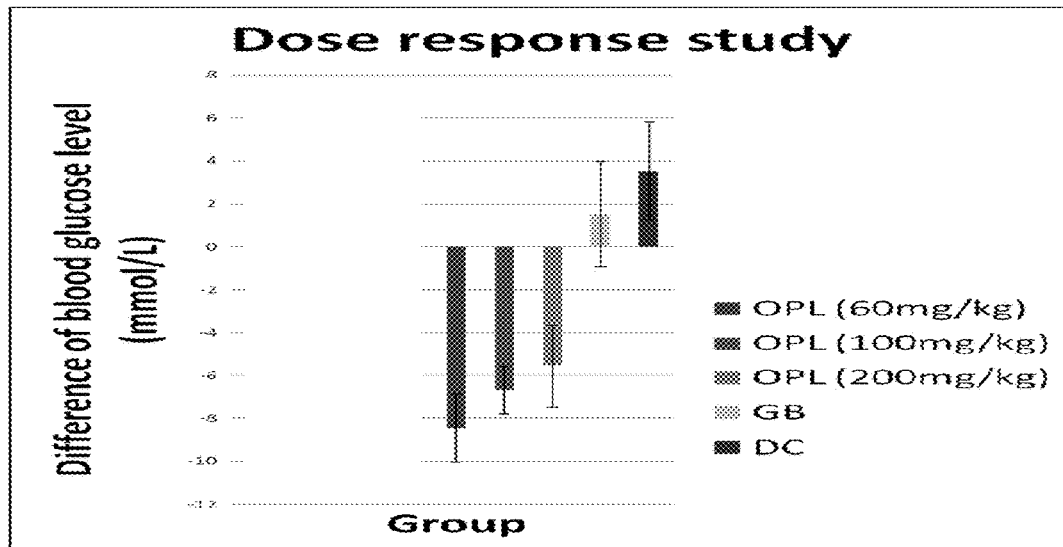

Plasma concentration of glucose was measured at different time intervals in diabetic and control rats (DC and NC) together with treated groups with different dose and treated with glibenclamide group (GB). Bar represent mean±SE of ten rats for each group (n=10). $p < 0.01$ Fig 1: The effect of dietary PALM LEAF EXTRACT on blood glucose of rats.

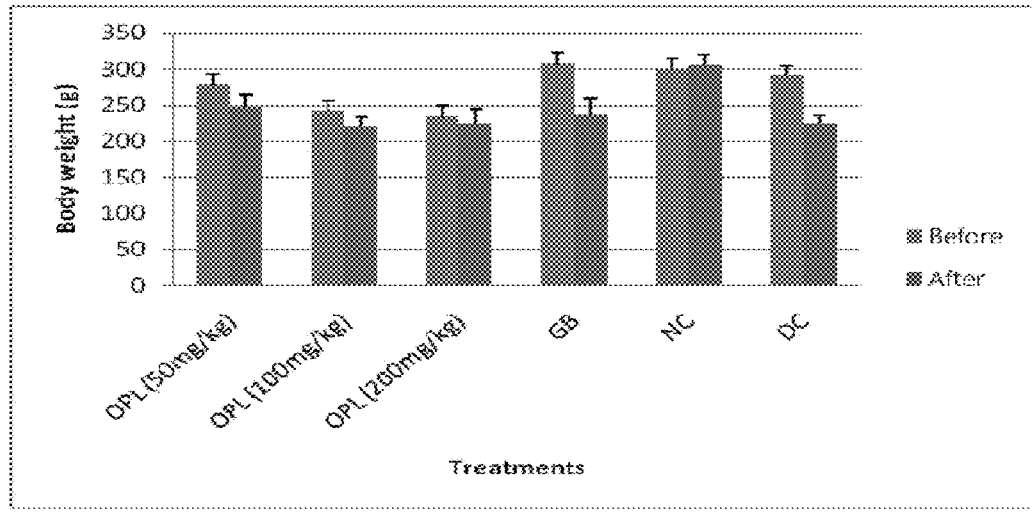

OPL = (50-200 mg/kg) Oil Palm leaf Extract given to diabetic rats per day
GB = Glibenclamide treated diabetic rats
NC or NF = Normal control or Normal Feed Rats
DC = Diabetic negative control untreated rats
Before: 0 weeks,          After: 8 weeks of study

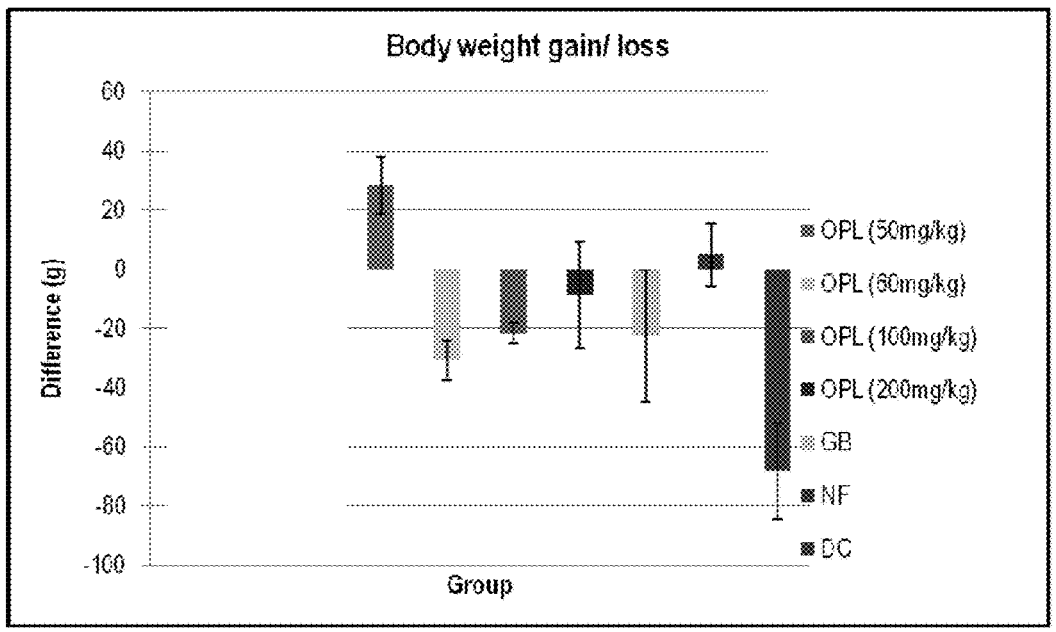

Fig 2: Effect of PLE on body weight in rats. Results expressed as mean±S.E of ten rats for each group (n=10). $p < 0.05$
The number of surviving diabetic rats (out of 10) at the end on 3 months study.

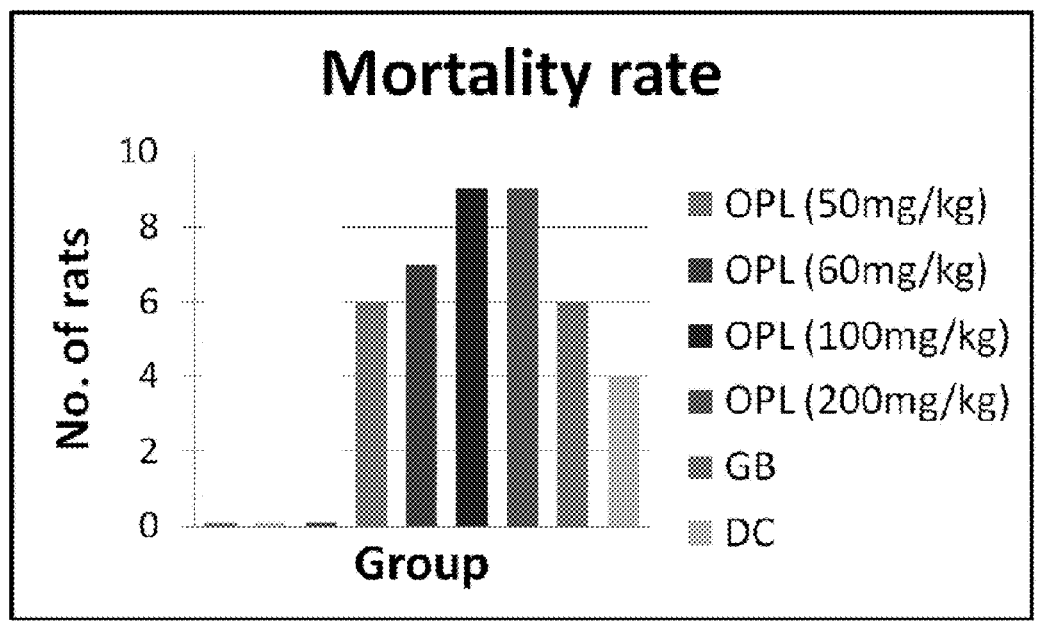
OPL = (50-200 mg/kg) Oil Palm leaf Extract given to diabetic rats per day
GB = Glibenclamide treated diabetic rats
DC = Diabetic negative control untreated rats
Number of surviving diabetic rats (out of ten rats) for each group (n=10).
Fig 3: Effects of PLE on the number of surviving diabetic rats (initial number 10) at the end on 3 months study.

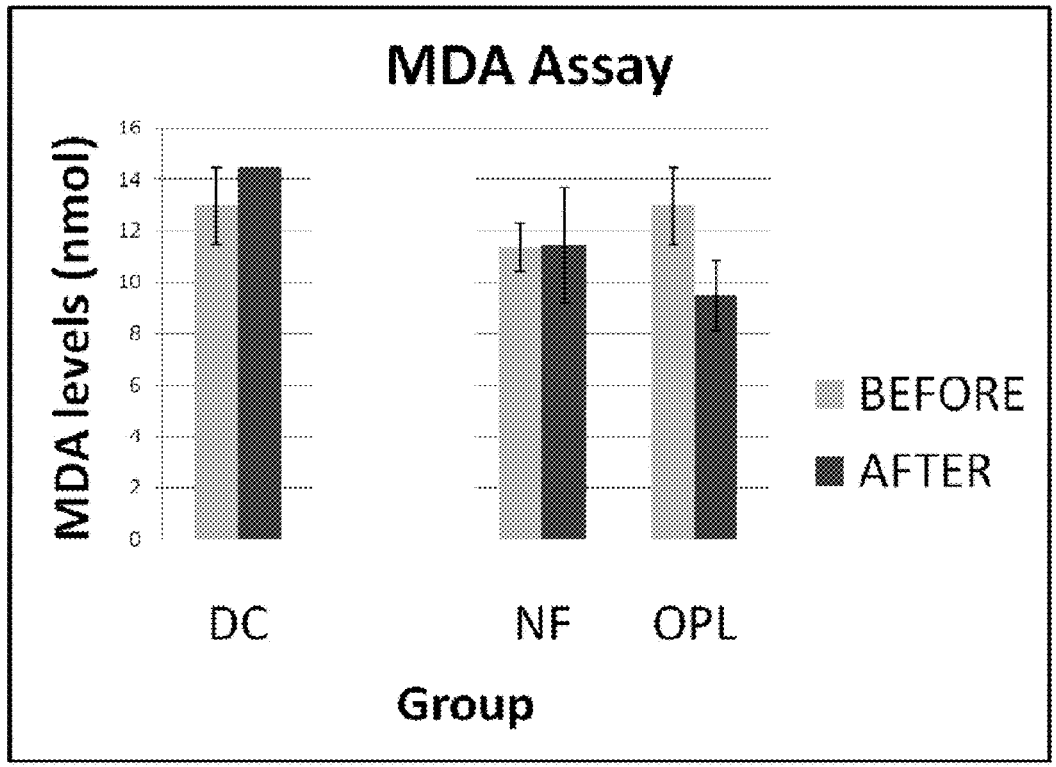

OPL = (50-200 mg/kg) Oil Palm leaf Extract given to diabetic rats per day
GB = Glibenclamide treated diabetic rats
NF = Normal control /Feed Rats
DC = Diabetic negative control untreated rats
Before: 0 weeks,					After: 8 weeks of study Fig 4: Effects of PLE on erythrocytes malondialdehyde MDA levels (a marker of lipid peroxidation and oxidative status) of rats at the end on 8 weeks study.

Histopathology observations on Kidney and liver

| Treatment | KIDNEY<br>Percentage of damage glomerulus | LIVER<br>PERCENTAGE OF NECROTIC LIVER & INFLAMMATION |
|---|---|---|
| OPL 50mg/kg | 31.7% [a] | 24.40 ± 2.76 [a] |
| OPL 100mg/kg | 25.4% [a] | 25.20 ± 1.94 [a] |
| OPL 200mg/kg | 40.1% [a] | 34.73 ± 1.50 [a] |
| NC | 30.0% [a] | 54.00 ± 2.08 [b] |
| DC | 80.2% [b] | 88.00 ± 1.53 [c] |

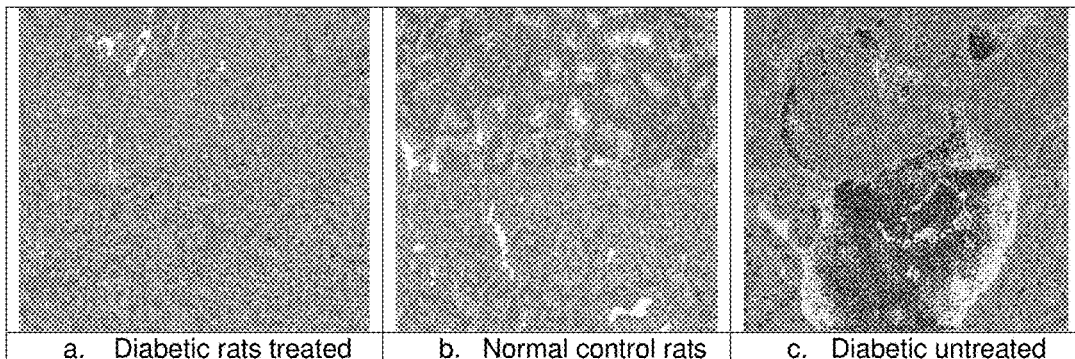

| a. Diabetic rats treated with palm leaves revealing a normal kidney glomerulus and tubule | b. Normal control rats revealing a normal glomerulus and tubule | c. Diabetic untreated control rats shows severe damage to kidney glomerulus and tubules |
|---|---|---|

Photomicrograph, kidney of rat from EC (a) and OPL (b) groups at necropsy. At higher magnification (H&E, x 400) Photomicrograph, kidney of rat from NC (c) and DC (d) groups at necropsy. At higher magnification (H&E, x 400)

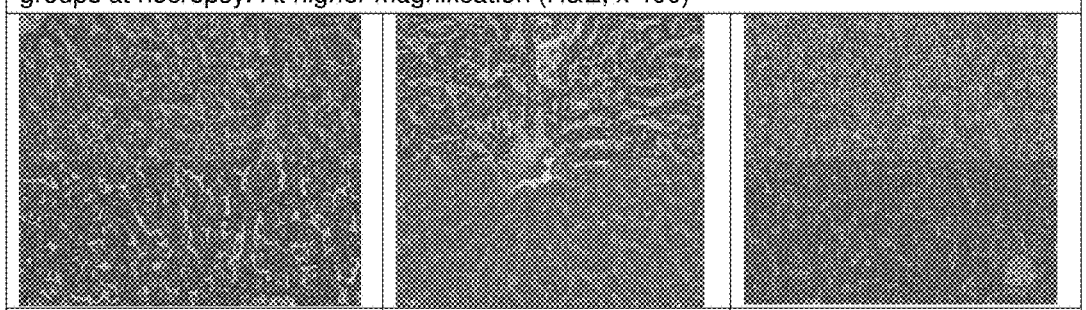

| a. Diabetic rats treated with palm leaves showed low levels of necrotic liver cells, inflammation and little or no vacuolation | b. Normal control rats showed few inflammation and necrosis | c. Diabetic untreated control rats showed 80 - 90% of damaged necrosis and inflammation and vacuolation |
|---|---|---|

Fig 5: the effects of dietary PALM LEAF EXTRACT on the histopathology of the kidneys and liver tissues of diabetic rats

ANTI-DIABETIC NUTRACEUTICAL COMPOSITION FROM PALM LEAF EXTRACT

CROSS-REFERENCED TO RELATED APPLICATIONS

This application is a divisional of U.S. patent application Ser. No. 13/260,188, which is the national stage of international application no. PCT/MY2009/00041, filed Mar. 24, 2009. The foregoing applications are incorporated herein by reference.

FIELD OF INVENTION

The present invention relates to a nutraceutical with significant anti-diabetic property. The disclosed comestible composition can reduce the blood sugar in diabetics, protects against diabetic oxidative stress and help prevent diabetic complications, and contains extract from palm leaf.

BACKGROUND OF INVENTION

Diabetes mellitus is a carbohydrate metabolism disorder (genetic or lifestyle causes), resulting in high blood glucose levels (hyperglycemia), due to either defects in insulin secretion (Type 1) or insulin action (type 2 and gestational). The acute signs of diabetes are excessive urination, excessive thirst, impaired vision, weight loss, and tiredness. Insulin injection is the general treatment for type 1 diabetes, while type 2 can be controlled through diet, exercise, medications and insulin supplementation.

Diabetes complications include hypoglycemia, ketoacidosis, or nonketotic hyperosmolar coma (acute) and dangerous long-term complications such as cardiovascular disease (doubled risk), chronic renal failure, retinal damage (leading to blindness), nerve damage, and microvascular damage (leading to erectile dysfunction) and poor wound healing (leading to gangrene and possibly amputation). Adequate control of blood sugar, blood pressure and body weight, can improve the risk of diabetic complications. Diabetes is the main cause of non-elderly adult blindness, non-traumatic amputation, and renal malfunction. Diabetes causes increased protein glycation and the formation of early glycation products and advanced glycation end products (AGEs) which are major factors responsible for the complications of diabetes.

Metabolites from some plants have been proven to possess anti-diabetic properties. A few anti-diabetic products containing plant metabolites as the active ingredients have been developed. For example, polyphenol product extracted from green tea (Polyphenon 60) and antiglycation agent (aminoguanidine) are commercially available. Guava leaf extracts, gallic acid, catechin and quercetin are potent antiglycation agents, which can be of great value in the preventive glycation-associated complications in diabetes. U.S. Pat. No. 6,984,666 provides a novel method for the preparation of a unique profile of primary aliphatic alcohols, having 24 to 30 carbon atoms, from the wax secreted by the insect *Ericerus pela*. The polycosanol composition is comprised primarily of the four primary aliphatic alcohols, tetracosanol, hexacosanol, octacosanol and triacontanol, for use in the prevention and treatment of obesity, syndrome X, diabetes, hypercholesterolemia, atherosclerotic complications, ischemia and thrombosis.

WO 2008134828 discloses a method for obtaining stable pharmaceutically acceptable salts of isolated or essentially pure diterpenoic tetrahydropyran, such as steviol-19-glucuronide, steviol, stevioside and rebaudioside in the treatment of cardiovascular disorders or vascular disease.

WO 2008059310 and WO 2008142702 provide a method for producing water based herbal extracts from *Cinnamomun zeylanioum* plant species with hypoglycemic activity, for prevention or management of diabetes by inhibiting the glucose absorption in the intestine and by mimicking and potentiating the insulin activity.

EP 1738658 claims a composition for inhibiting hyperglycaemia and AGE (advanced glycated end products) generation made from an acerola leaf extract and/or a processed product thereof.

EP 1331858 provides a source of delta-tocotrienol and/or -tocopherol acts synergistically with an antioxidant source comprising polyphenols, to effect suppression of LDL oxidation in serum. The combination of these two antioxidant sources has wide-ranging applications in treatment of medical conditions arising from free radical generation, including arteriosclerosis and cancer.

WO 2006053379 discloses a nutraceutical composition including one or more extracts of one or more plant components, the one or more extracts providing a combination of phytonutrient materials, the type and amount of which are in excess of a minimum value predetermined to provide a therapeutically or prophylactically desirable effect.

SUMMARY OF INVENTION

Accordingly, the present invention provides a composition with anti-diabetic property for diabetic management and prevention against oxidative stress, retarding diabetes related complications, retarding diabetes related organ degeneration and effective to hinder or prevent ailments or conditions resulting from, or exacerbated by, a chronic increase in blood sugar including: tissue degeneration, cardiovascular disease, kidney disfunction, loss of cognitive function, weight loss, visual impairment, and vasomotor symptoms, comprising an extract from leaves of Palmae family.

The present invention consists of several novel features and a combination of parts hereinafter fully described and illustrated in the accompanying description and drawings, it being understood that various changes in the details may be made without departing from the scope of the invention or sacrificing any of the advantages of the present invention.

BRIEF DESCRIPTION OF THE DRAWINGS

The present invention will be fully understood from the detailed description given herein below and the accompanying drawings which are given by way of illustration only, and thus are not limitative of the present invention, wherein:

FIG. 1 is a graph showing the effect of PALM LEAF EXTRACT on Blood sugar level in diabetic rats.

FIG. 2 is a graph showing the effect of PALM LEAF EXTRACT on the body weight of diabetic rats.

FIG. 3 is a graph showing the effect of PALM LEAF EXTRACT on mortality rate of diabetic rats.

FIG. 4 is a graph showing the effects of dietary PALM LEAF EXTRACT on erythrocytes malondialdehyde MDA levels (a marker of lipid peroxidation and oxidative status) of rats at the end on 8 weeks study.

FIG. 5 is of plates showing the effects of dietary PALM LEAF EXTRACT on the histopathology of the kidneys and liver of diabetic rats.

DETAILED DESCRIPTION OF THE PREFERRED EMBODIMENTS

The present invention relates to nutraceutical with significant anti-diabetic property. The disclosed comestible composition can reduce the blood sugar in diabetics, protects against diabetic oxidative stress and help prevent diabetic complications, and contains extract from palm leaf. Hereinafter, this specification will describe the present invention according to the preferred embodiments of the present invention. However, it is to be understood that limiting the description to the preferred embodiments of the invention is merely to facilitate discussion of the present invention and it is envisioned that those skilled in the art may devise various modifications and equivalents without departing from the scope of the appended claims.

The present invention aims to provide a nutraceutical composition which is effective in lowering the blood glucose and improve oxidative status in diabetes mellitus and have anti-diabetic properties that protect against diabetic complications, retarding diabetes related organ degeneration and effective to hinder or prevent ailments or conditions resulting from, or exacerbated by, a chronic increase in blood sugar including: tissue degeneration, cardiovascular disease, kidney degeneration, loss of cognitive function, weight loss, visual impairment, and vasomotor symptoms which contains extract from palm leaf.

At least one of the preceding objects is met, in whole or in part, by the present invention, in which one of the embodiment of the present invention a composition with anti-diabetic property comprising aqueous or alcoholic extract from palm leaf.

The following detailed description of the preferred embodiments will now be described in accordance with the attached drawings, either individually or in combination.

One skilled in the art will readily appreciate that the present invention is well adapted to carry out the objects and obtain the ends and advantages mentioned, as well as those inherent therein. The embodiment describes herein is not intended as imitations on the scope of the invention.

The term "pharmaceutically effective amount" used herein through out the specification refers to the amount of the active ingredient, the extract, to be administered orally to the subject to trigger the desired effect without or causing minimal toxic adverse effect against the subject. One skilled in the art should know that the effective amount can vary from one individual to another due to the external factors such as age, sex, diseased state, races, body weight, formulation of the extract, availability of other active ingredients in the formulation and so on.

It is important to note that the extract used in the disclosed method in this embodiment is derived from the plant species of Arecaceae family. The extracts obtained from the above-mentioned plant species are suitable to be incorporated into edible or topical products, or as capsules, ointments, lotions and tablets.

The desired compounds to be extracted from the alcohol/aqueous extracts of are mainly constituted of, but not limited to, biophenols, proteins, lipids, saccharides, minerals and small peptides. Due to polarity of these compounds, the polar solvent such as water, alcohol or acetone is found to be effective in extracting these desired compounds from the plant matrix.

Another embodiment of the present invention involves a comestible and/or topical composition with anti-diabetic property comprising alcohol/aqueous extracts derived from the leaves of Palmae family using an appropriate extraction solvent. The comestibles mentioned herein can be any common daily consumed processed food such as bread, noodles, confections, chocolates, beverages, and the like. One skilled in the art shall appreciate the fact that the aforesaid extract can be incorporated into the processed comestibles, capsules, tablets or topical medicine during the course of processing. Therefore, any modification thereon shall not depart from the scope of the present invention.

As setting forth in the above description, the composition with anti-diabetic properties comprising aqueous or alcoholic extract from leaves of Palm species. Apart from that the composition may further comprise extract derived from the leaves of Palm species. Preferably, the plant is any one or combination of the plant species of, *Elaeis guineensis, Elaeis oleifera, Phoenix dactylifera* and *Cocos nucifera*. The inventors of the present invention found that the water/alcohol extract derived from the aforementioned species possesses both acceptable taste that confers the derived extract to be comfortably incorporated with the comestibles product, capsules, tablets or topical medicine with minimal additional refining process.

According to the preferred embodiment, the extract to be incorporated into the comestibles and medicine can be acquired from any known method not limited only to the foregoing disclosed method. Following another embodiment, the extract is prepared in a concentrated form, preferably paste or powdery form which enables the extract to be incorporated in various formulations of the comestibles, capsules, tablets or topical products.

In line with the preferred embodiment, the extract shall be the plant metabolites which are susceptible to an extraction solvent. The compounds and small peptides with the anti-diabetic and organ health-promoting properties are those metabolites with polarity in the alcohol/aqueous extracts. Therefore, the alcohol/aqueous extracts of leaves of Palmae family is preferably derives from the extraction solvent of water, alcohol, acetone, chloroform, liquid $CO_2$ and any combination thereof.

In view of the prominent property of promoting anti-diabetic activity and general healthcare of the body system by the extracts in a subject, further embodiment of the present invention includes a method comprising the step of administrating orally or topically to the subject an effective amount of an extract derived from palm spp. leaves.

The following example is intended to further illustrate the invention, without any intent for the invention to be limited to the specific embodiments described therein.

EXAMPLE 1

Adult normal and streptozotocin-induced diabetic male Sprague Dawley rats were randomly divided into groups. Palm leaf aqueous and alcoholic extracts (PLE) were fed to normal and STZ-induced diabetic rats at 50-200 mg/kg for 8 weeks. Blood sugar levels from fasting rats were monitored weekly. Untreated rats were used as negative control and glibenclamide (30 mg/kg) treated rats used as positive control. PLE helped normalise blood glucose levels (FIG. 1), maintained the body weight (FIG. 2), lipid profile (Table 1), antioxidative status (FIG. 4) and improved the mortality (FIG. 3) of diabetic rats in a dose dependent manner. Histological observations also showed PLE provided organ protective effects to the heart, liver, kidneys (FIG. 5) and prevented against macro vascular complication in diabetic rats. At the doses used PLE showed no adverse or chronic toxicity effects in normal or diabetic rats.

Streptozotocin was known to destroy insulin producing pancreatic cells, the STZ-treated rat model would appear to represent a good experimental NIDDM diabetic state. Induction of diabetes in the experimental rats was confirmed by the presence of a high fasting plasma glucose level. The effect of ethanolic extract of PLE on fasting blood glucose levels of normal and STZ induced rats are presented in FIG. 1. The difference between the experimental and control rats in lowering the fasting plasma glucose levels were statistically significant ($p<0.05$) in diabetic rats and was more than the glibenclamide treated rats. Daily administration of PLE to diabetic rats significantly reduced blood glucose level after 15 days of treatment in comparison to control diabetic rats. In contrast to STZ-induced diabetic rats, no significant change was observed in blood glucose levels of normal rats. The rats were normoglycemic throughout the experimental period. The antidiabetic activity was found to be dose dependent as there was a significant difference between 50, 100 and 200 mg/kg extract treated groups. Dose 100 mg/kg showed the optimum dose as compared to the others.

EXAMPLE 2

Diabetes induced with STZ is associated with the characteristic loss of body weight which is due to the increment of muscle wasting. Normal rats gained weight throughout the experimental period. The body weight changes were not significant in normal rats (with or without PLE). Administration of PLE to normal rats did not significantly alter body weight and plasma glucose during the 15 days period. In contrast, the control diabetic rats showed significant weight loss when compared to both normal rats and PLE treated diabetic rats by the end of treatment at day 15 (FIG. 2). Both the diabetic rats and PLE treated diabetic rats had lower body weights when compared to normal rats. Significant changes in body weight were only observed in the glibenclamide treated group (FIG. 2).

The weight loss that occurred in STZ-induced diabetic rats was attenuated by PLE treatment. In addition, PLE treatment resulted in a beneficial effect on mortality rate. Survival data were obtained from day 1, 7 and 15. The PLE treated groups at dose 100 and 200 mg/kg showed lower mortality (one out of ten) and was similar to the normal control rats group, whilst the control diabetic group had very high mortality rate (six out of ten). The results showed a statistically significant increased in survival rate for treated diabetic groups. These changes may be a reflection of the improved health of the PLE treated groups.

EXAMPLE 3

A significant decrease ($p<0.05$) in serum triglycerides was observed in diabetic rats after the treatment period when compared to normal and STZ-induced diabetic rats with PLE. TG levels in PLE treated diabetic rats were found to be similar with the control normal group and significantly higher compared to diabetic groups (Table 1).

Liver and kidney toxicity of the intervention were assessed through serum measurements of a liver panel i.e. total protein, AST, ALT and creatinine. This study showed that PLE effectively inhibited the incidence of diabetic nephropathy. Diabetic nephropathy is mainly associated with excess in urinary albumin excretion, abnormal renal function as represented by the abnormality in serum creatinine. Proteinuria is a major predictor of glomerular injury and elevated of protein excretion are selective markers of progressive nephropathy. STZ-induced diabetic rats are characterized by the development of proteinuria and it has been shown that STZ has no long-term direct effects on the kidney, but STZ has secondary effects on the kidney as a result of the development of diabetes mellitus.

Measurement of enzymic activities of aminotransferases (ALT and AST) is of clinical and toxicological importance as changes in their activities are indicative of tissue damage by toxicants or in disease conditions. Aminotransferases, such as alanine aminotransferase (ALT) and aspartate aminotransferase (AST), measure the concentration of intracellular hepatic enzymes that have leaked into the circulation and serve as a marker of hepatocyte injury. AST and ALT activities in serum of the normal and PLE treated diabetic groups were significantly lower than that of the untreated diabetic animals.

Diabetic rats treated with PLE showed significant ($p<0.05$) beneficial effects on serum total protein and creatinine (Table 1). Total protein and creatinine levels were significantly decreased in diabetic rats as compared to normal and treated rats. Recovery of serum total protein, AST, ALT and creatinine levels of diabetic rats towards the normal levels showed that the PLE has beneficial and no adverse effect on liver and kidney functions.

TABLE 1

The effect of *Elaies guineensis* ethanolic extract on biochemical parameters

| TREATMENT | TOTAL PROTEIN (g/dl) | TRIGLYCERIDES (mg/dl) | AST (U/L) | ALT (U/L) | Creatinine (µmol/L) |
|---|---|---|---|---|---|
| 50 mg/kg | 77.50 ± 0.76* | 2.02 ± 0.23* | 228.4 ± 13.4* | 78.34 ± 9.37* | 64.50 ± 1.70 |
| 100 mg/kg | 74.56 ± 1.49* | 1.65 ± 0.49* | 225.0 ± 13.3* | 79.60 ± 7.69* | 71.11 ± 4.48 |
| 200 mg/kg | 71.88 ± 0.64* | 2.34 ± 0.28* | 261.6 ± 5.9* | 64.85 ± 1.27* | 63.13 ± 2.02 |
| DC | 62.50 ± 5.94 | 0.59 ± 0.17 | 439.1 ± 27.2 | 129.8 ± 15.1 | 57.33 ± 5.33 |
| CN | 75.38 ± 0.59* | 1.55 ± 0.09 | 211.1 ± 8.5* | 53.56 ± 3.75* | 67.38 ± 2.05 |

AST—Aspartate aminotransferase,
ALT—Alanine aminotransferase.
Data is expressed as mean ± SEM (n = 10)
*p < 0.05, as compared to control diabetic Diabetes is normally accompanied by increased risk factors such as hyperglycemia, dyslipidemia, hypertension, decreased fibrinolytic activity, increased platelet aggregation, and severe atherosclerosis. New nutraceuticals or drugs can be developed for treatment of diabetes from PLE without negative side effects at the dose given, that can reduce the risk of diabetes.

These results strongly showed that PLE is very useful in the alleviation of diabetic complications as well as in the prevention of the development of atherosclerosis and nephropathy in diabetic patients. Certain flavonoids exhibit hypoglycaemic activity and they are also known to help regenerate beta cell of the pancreas. Histological tissue observations and the significant antidiabetic effect of PLE indicates that this effect.

The invention claimed is:
1. A method of treating a diabetic subject, the method comprising:
   i. providing a composition comprising a pharmaceutically effective amount of a substance having an anti-diabetic property, wherein the substance is palm leaf extract which includes biophenols, proteins, lipids, saccharides, minerals and small peptides, wherein the extract is obtained from leaves of a palm tree species, and wherein the palm tree species is selected from the group consisting of *Elaeis guineensis, Elaeis oleifera,* and *Phoenix dactylifera* or a combination thereof; and
   ii. administering the composition to the diabetic subject to treat diabetes.
2. The method as claimed in claim 1, wherein the extract is an aqueous, an aqueous alcoholic or a polar extract.
3. The method as claimed in claim 1, comprising administering a pharmaceutically effective amount of the palm leaf extract sufficient to reduce blood sugar in the diabetic subject.
4. The method as claimed in claim 1, comprising administering a pharmaceutically effective amount of the palm leaf extract sufficient to inhibit diabetic oxidative stress in the diabetic subject.
5. The method as claimed in claim 1, comprising administering a pharmaceutically effective amount of the palm leaf extract sufficient to inhibit diabetic complications in the diabetic subject.
6. The method as claimed in claim 1, comprising administering a pharmaceutically effective amount of the palm leaf extract sufficient to inhibit tissue degeneration, cardiovascular disease, kidney dysfunction, loss of cognitive function, weight loss, visual impairment, and vasomotor symptoms in the diabetic subject.
7. The method as claimed in claim 1, wherein the palm leaf extract is an alcoholic extract.
8. The method as claimed in claim 1, wherein the palm leaf extract is an ethanol extract.
9. The method as claimed in claim 1, wherein the pharmaceutically effective amount is 50-200 mg/kg.
10. The method as claimed in claim 9, wherein the composition is administered daily for at least 15 days.

* * * * *